United States Patent [19]

Kitahara

[11] Patent Number: Plant 6,756

[45] Date of Patent: Apr. 25, 1989

[54] PLUM TREE

[75] Inventor: Larry Kitahara, Clovis, Calif.

[73] Assignee: Kitahara Farms, Reedley, Calif.

[21] Appl. No.: 37,345

[22] Filed: Apr. 13, 1987

[51] Int. Cl.[4] ..... A01H 5/03

[52] U.S. Cl. ..... Plt./38

[58] Field of Search ..... Plt./38

*Primary Examiner*—Robert E. Bagwill

*Attorney, Agent, or Firm*—Townsend & Townsend

[57] ABSTRACT

The present invention relates to a plum tree and more particularly to a new and distinct variety broadly characterized by a very upright, simi-open tree which bears a large, symmetrical, firm fruit of sweet taste and yellow-amber flesh and an attractive blue-black skin color. The new variety generally resembles the Friar (unpatented) variety, but under the ecological conditions described, generally ripens during the last two weeks of August, three to four weeks later than the Friar variety — a late date for a mid-season plum. The fruit is of good eating and keeping quality and is suitable for local and long distance markets.

1 Drawing Sheet

The new variety bears the cultivar name Royal Diamond.

I discovered the instant variety of plum trees as a three year old tree in a block of hybrid seedlings owned by me on my farm at Kingburg, southern San Joaquin Valley, Calif. The new variety was grafted on existing plum stocks, and the asexually reproduced trees and fruit were true to the original seedling in all respects.

The new variety generally resembles the Friar plum variety (unpatented), having some of the same characteristics such as large size, dark skin coloration, slightly wavey skin surface, and an upright growth. The instant variety, however, matures three weeks to one month later than the Friar plum variety. The date of full bloom for the new variety is late in relation to other varieties of mid-season bloom timing such as Friar and Santa Rosa, commencing bloom March 2 and reaching full bloom by March 14, under the ecological conditions described. The new variety more closely resembles the plum variety Simka (U.S. Plant Pat. No. 1,882) in bloom time. The tree form for the new variety is very upright, especially in comparison with other late maturing varieties such as Casselman and Roysum (U.S. Plant Pat. No. 2,619.) The growth habit is not as dense and spreading as the above varieties, being intermediate in form between the dense, spreading Casselman type and the upright, open Friar plum tree.

The accompanying photograph shows the characteristics of the whole fruit in skin color and form, and a characteristic fruit divided at its suture plane showing the flesh and pit, as well as the bloom, and some characteristic leaves.

Referring now more specifically to the pomological characteristics of this new and distinct variety of plum tree, the following was made from fruit of firm commercial maturity under the ecological and conditions prevailing near Kingsburg, southern San Joaquin Valley, Calif. All color plate identifications are by reference to Maerz and Paul "Dictionary of Color", published 1950.

TREE

General: Very upright, medium vigor and medium density. Productive. Hardy for California conditions.

Trunk: Medium surface texture. Older bark greyish-brown (15-J-8) with numerous lenticels. Trunk of average diameter for species.

Branches: Mature one year old shoots brown in color (15-H-9). New shoots green (20-J-8). Branches medium in size with smooth surface texture.

Leaves:

*Size.*—Measurements from leaves at midpoint of actively growing shoots. Average length 13.0 cm, average width 6.4 cm. Moderately large in size.

*Form.*—Broadly obovate. Leaf apex acuminate with a significant number of tips reflexed.

*Color.*—Upper surfaces dark green (24-L-6). Lower surfaces grey-green (22-E-4). Mid-vein on upper surface light yellow-green (19-H-3) about 1 mm wide.

*Leaf margin.*—Dull serrate, more sharply serrate near basal end. Moderately deep serrations, double to occasionally triple. Regular. Leaf margin only moderately undulate along outer margins. Leaf blades most often relatively flat.

*Petiols.*—Moderately long, 14–15 mm, 1–2 mm in thickness. Greenish (18-G-5) on under side, light brown along petiole groove (15-H-2).

*Stem glands.*—2 to 3 medium sized globose glands, often 2 at base of leaf blade and one on petiole, all borne on short stalks. Color green (20-J-7).

*Stipules.*—1 to 2 at base of petiole, relatively small size, 4 to 6 mm in length. Narrow, often less than 1 mm, and greenish in color (20-G-5). Usually persistent.

Flower buds: Hardly for California conditions. Small size, conic, slightly pubescent. Color brown-grey (15-L-8).

Flowers: Bloom description made Mar. 10, 1984.

*Time of bloom.*—Late in relation to other plum varieties growing in same area. First bloom Mar. 2, 1984, full bloom Mar. 12, 1984.

*Size of flowers.*—Medium to slightly above. Average 18 to 20 mm in diameter when fully expanded. Bloom abundant, often 7 to 9 flowers per node.

*Petals.*—Medium to slightly above. Broadly ovate in form, 8 to 9 mm in width, 9 to 10 mm in length.

Petals comewhat cupped inward even at full maturity. Color white (1-A-1), Petal margins slightly undulate.

*Pedicel.*—Medium length, 7 to 8 mm. Color light green (17-K-4). Glabrous.

*Nectaries.*—Color brownish-yellow (12-J-8) on mature flowers. Young nectaries brown-orange (12-K-10).

*Anthers.*—Medium in size and plumpness. Red-orange in color dorsally (5-F-12), light buff ventrally (10-G-7). Pollen abundant, yellow (9-L-5).

*Stamens.*—Moderately long, color white (1-A-1).

*Pistil.*—Moderately long, about 10 mm when fully extended. Very light green in color (17-D-2).

FRUIT

Described at firm, full commercial maturity, Aug. 19, 1983. First pick Aug. 17, 1983, last pick Aug. 27, 1983.

Size: Uniform, large size. Average cheek diameter 59 mm, average suture diameter 58 mm, average axial diameter 51 mm.

Form: Uniform, very symmetrical. Almost perfectly round in axial aspect. Fruit moderately oblate in lateral aspect.

Suture: A small dark line extending from base to to apex, 1 to 2 mm in width. Suture line blends well with surrounding coloration, becoming more distinct with advancing maturity.

Ventral surface: Rounded. Very slightly lipped, usually more apparent on basal shoulder. Very symmetrical.

Stem cavity: Rounded. slightly oval in suture plane. Average width 14.0 mm, average length 16.8 mm. Moderately deep 10 to 11 mm.

Base: Rounded, slightly truncate. Base at right angle to fruit axis.

Apex: Short, slightly truncate. Pistil point spical and slightly depressed.

Stem: Medium length, 10 to 12 mm. Thickness 1.5 to 2.0 mm. Color light green (18-H-4) to brown (14-C-12).

Skin: Moderately thick, only slightly acid. Tenacious to flesh. No observed tendency to crack. Some light skin rippling apparent, especially on large fruit.

Skin color: An attractive blue-black varying to dark blood red over 95 to 100 percent of the fruit surface (48-H-9). Occasional areas a lighter purple (8-J-6) where covered by leaf or stem. Moderate flecking over apex and apical shoulder. Scant flecking over basal areas.

Flesh color: Light yellow-amber (11-J-4) with no red in flesh. Slightly darker amber just under skin 3 to 4 mm (11-J-6). Slightly darker amber also in pit cavity (11-J-7).

Texture: Firm, very slightly coarse, juicy.

Fibers: Moderately long, average in numbers. Tender and fine.

Ripening: Ripens evenly.

Flavor: Sweet, well balanced. Pleasant.

Aroma: Slight.

Eating quality: Very good.

STONE

Semi-cling. Free along ventral suture, adheres to flesh along dorsal suture and over half of sides.

Size: Medium to small. Average length 21 mm, average width 17 mm, average breadth 10.5 mm.

Fibers: Short.

Form: Roughly oval to ovate.

Base: Rounded on ventral suture edge, slightly truncate on dorsal suture edge. Base usually oblique to stone axis, shorter on ventral suture side.

Hilum: Small, narrow, oblong.

Apex: Rounded. Tip very small and cuspidate.

Sides: Slightly unequal.

Stone surface: Sides pebbly. Usually one strong groove running roughly parallel to ventral edge, 2 to 4 mm back from edge, and extending from base nearly to apex. Occasional short low ridges over apical shoulder.

Ventral edge: Moderately thick, occasionally with very low inconspicuous wing over apical shoulder.

Dorsal edge: Deep, moderately broad groove along dorsal edge from base to above suture midpoint. Groove at times discontinuous. Groove becomes shallow and narrow from above midpoint to stone apex. Apical shoulder often protruding.

Stone color: Color light buff (9-D-2).

Tendency to split: None observed.

Use: Fresh market for both local and long distance shipping.

Keeping quality: Good.

Resistance to disease and insects: No particular susceptibilities noted.

Shipping quality: No volume shipping yet tested.

I claim:

1. A new and distinct variety of plum tree substantially as described and illustrated, which generally resembles the Friar (unpatented) variety in the very upright growth of the tree and by some characteristics of its fruit, but can be readily distinguished therefrom and is an improvement thereon by having a bloom timing which is later than the Friar and Santa Rosa varieties and resembles the Simka (U.S. Plant Pat. No. 1,882) variety, and by ripening of its fruit three to four weeks later than the Friar variety.

* * * * *

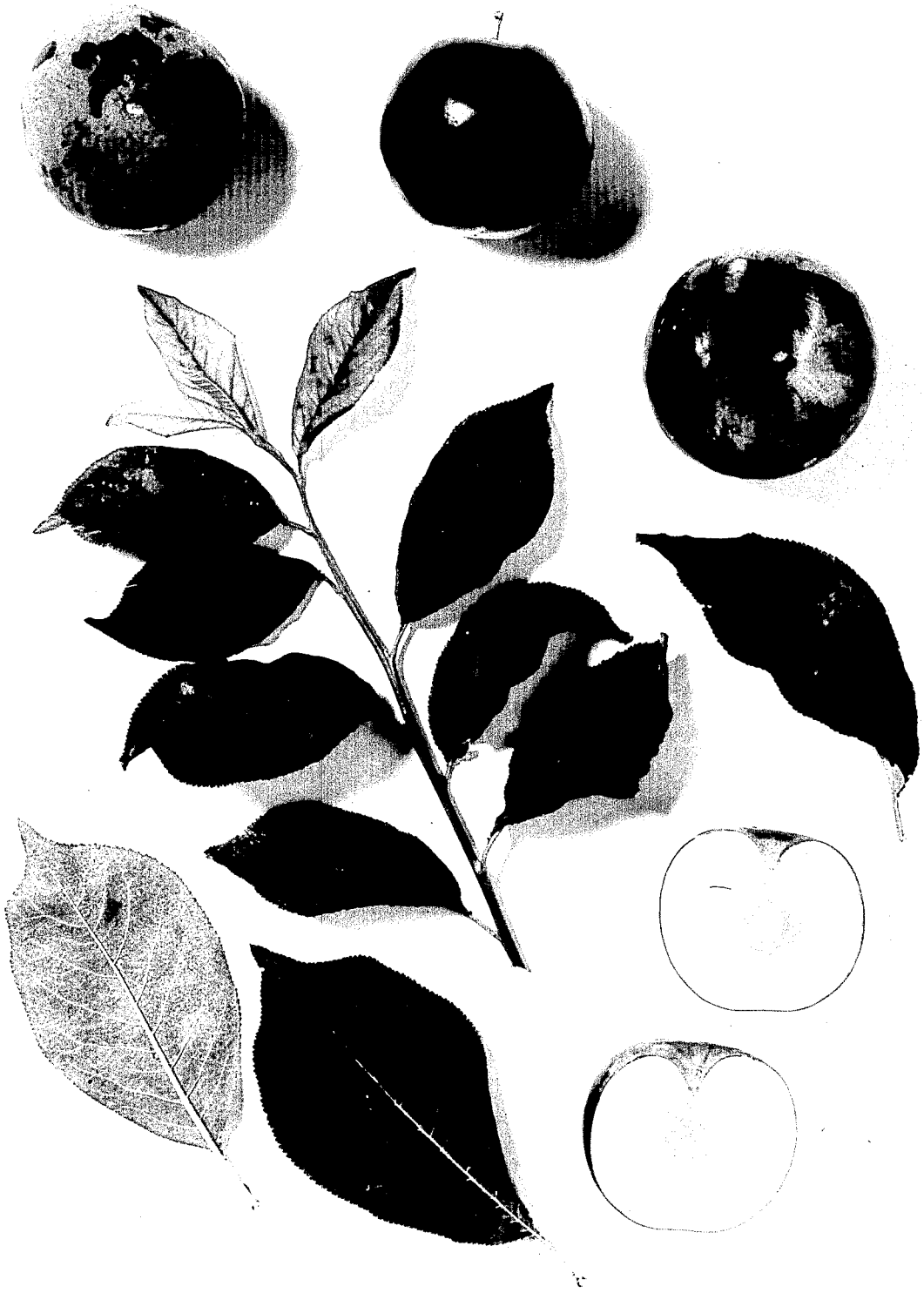

U.S. Patent Apr. 25, 1989 Plant 6,756